United States Patent [19]
Kambe et al.

[11] Patent Number: 6,090,988
[45] Date of Patent: Jul. 18, 2000

[54] METHOD FOR RECOVERING ALKYL VINYL ETHER

[75] Inventors: Hideyuki Kambe, Izumiotsu; Hitoshi Yano, Suita; Yuuji Shimasaki, Otsu, all of Japan

[73] Assignee: Nippon Shokubai Co., Ltd., Osaka, Japan

[21] Appl. No.: 09/040,967

[22] Filed: Mar. 18, 1998

[30] Foreign Application Priority Data

Mar. 26, 1997 [JP] Japan ..................................... 9-073635

[51] Int. Cl.⁷ ...................................... C07C 41/00
[52] U.S. Cl. .......................... 568/687; 568/698; 502/240; 502/243; 502/250; 502/341
[58] Field of Search ..................................... 568/687, 698; 502/240, 243, 250, 341

[56] References Cited

U.S. PATENT DOCUMENTS

| | | |
|---|---|---|
| 5,124,005 | 6/1992 | Yang et al. . |
| 5,650,544 | 7/1997 | Ariyoshi et al. . |
| 5,773,669 | 6/1998 | Shimasaki et al. ...................... 568/687 |

FOREIGN PATENT DOCUMENTS

| | | |
|---|---|---|
| 0701986 | 3/1996 | European Pat. Off. . |
| WO95/04762 | 2/1995 | WIPO . |

*Primary Examiner*—James O. Wilson
*Attorney, Agent, or Firm*—Jordan and Hamburg LLP

[57] ABSTRACT

A reaction mixture in a gas form which is obtained by intramolecular dehydration of glycol ether in a gas phase is liquidized and collected by using as a collecting agent the glycol ether which is a raw material of the reaction mixture. The collected liquid thus obtained is continuously distilled by using a continuous distillation column so that a distillate containing alkyl vinyl ether and water is obtained, while a bottom product containing glycol ether is obtained. The distillate is left to stand in a separation vessel whereby separating into an oleaginous layer and an aqueous layer, so that alkyl vinyl ether is collected as the oleaginous layer. On the other hand, in the case where the bottom product contains water, the bottom product is continuously distilled together with an azeotrope former by using a continuous distillation column whereby a distillate containing an azeotrope of water and the azeotrope former, so that glycol ether is collected as a bottom product. By doing so, a method whereby alkyl vinyl ether as well as glycol ether which is the raw material and the collecting agent are efficiently collected, purified, and recovered is realized.

19 Claims, 4 Drawing Sheets

METHOD FOR RECOVERING ALKYL VINYL ETHER

FIELD OF THE INVENTION

The present invention relates to a method for recovering alkyl vinyl ether obtained by gas phase reaction. The alkyl vinyl ether is superior in reactivity, being a useful chemical compound widely applicable to various industrial fields, as raw material for synthetic resins, adhesives, various organic compounds such as glutaric aldehyde, and the like.

BACKGROUND OF THE INVENTION

Conventionally, alkyl vinyl ether has been produced by the following methods of two kinds: (1) the so-called Reppe method wherein acetylene in the liquid phase is caused to have addition reaction with alcohol under pressure with use of an alkaline catalyst; and (2) the so-called acetal method wherein acetal which is obtained by dehydration and compression of acetaldehyde and alcohol is de-alcoholated by thermal decomposition in the gas phase.

However, the Reppe method, though exhibiting a high reaction selectivity, has drawbacks such as complexity in reaction control and production control (operation control) including safeguard, from the following reasons: (1) it is an exothermic reaction whereby heat is greatly emitted; (2) acetylene which may possibly decompose and explode has to be dealt with under pressure; and (3) reaction performances such as the reaction selectivity or the reaction yield extraordinarily depend on concentrations of a raw material and a catalyst. On the other hand, the acetal method has drawbacks such as high producing costs, from the following reasons: (1) acetal as a raw material is difficult to obtain and costs high; and (2) an alcohol, which is by-produced to an equal molar number to that of an alkyl vinyl ether, has to be separated from the alkyl vinyl ether and purified, so that the alcohol is recovered to be used as a raw material for synthesis of acetal.

As a method wherein the above drawbacks are solved, the present applicant has before proposed a method for producing alkyl vinyl ether by intramolecular dehydration of glycol ether in the gas phase in the presence of a catalyst (the Japanese Publication for Laid-Open Patent Application No. 8-143497/1996 (Tokukaihei 8-143497)). Glycol ether, which is produced by reaction between alcohol and ethylene oxide, is easy to obtain and does not cost high. As to the producing process, no raw material other than glycol ether is necessary, and moreover, a reaction selectivity of not less than 90 mole percent is achieved by appropriately selecting a type of a catalyst and reactive conditions.

A gaseous reaction mixture (hereinafter referred to as reaction gas) obtained through the above process contains as by-products water, acetaldehyde and alcohol which are products of decomposition of glycol ether, and non-reacted glycol ether, in addition to alkyl vinyl ether as an object.

Alkyl vinyl ether generally has the following properties: (1) alkyl vinyl ether is an oleaginous compound which does not dissolve in water; (2) alkyl vinyl ether forms an azeotrope with water; (3) alkyl vinyl ether forms an azeotrope with an alcohol having an alkyl group in the same structure of that of the alkyl group of the alkyl vinyl ether (for example, alcohol produced by side reaction); and (4) since a vinyl group of alkyl vinyl ether has high reactivity, addition reaction wherein a compound having an acidic hydrogen atom or a basic hydrogen atom is added to the vinyl group tends to occur, and hence its properties easily change. Furthermore, glycol ether as a raw material and alcohol which is produced by side reaction generally have a property of forming an azeotrope with water.

Therefore, a reaction gas obtained through the aforementioned process is a mixture of compounds which have properties (physical properties) complicatedly relating to each other. For industrially and efficiently producing alkyl vinyl ether, it is necessary to efficiently liquidize and collect alkyl vinyl ether from a reaction gas, and further, to purify and recover alkyl vinyl ether and glycol ether which are raw materials.

However, the aforementioned publication does not particularly teach a method for efficiently collecting, purifying, and recovering alkyl vinyl ether from the reaction gas.

As to the reaction gas, an azeotrope of alkyl vinyl ether and water, though not always but depending on the type of alkyl vinyl ether, has an azeotropic point which is the lowest after the boiling point of acetaldehyde. In other words, it is difficult to liquidize alkyl vinyl ether, and hence, alkyl vinyl ether cannot be efficiently collected simply by liquidizing the reaction gas. Therefore, it is necessary to collect alkyl vinyl ether by diluting the reaction gas with a compound having a relatively high boiling point as diluent.

Furthermore, in the case where the reaction gas is collected with use of a collecting agent and the agent is a liquid compound widely used, such as an aliphatic-group hydrocarbon, an aromatic-group hydrocarbon, an ester of carbonic acid, or water, a solution after collection (hereinafter referred to as collected liquid) exhibits phase separation, separating into an oleaginous layer and an aqueous layer. Then, alkyl vinyl ether selectively dissolves in the oleaginous layer, while non-reacted glycol ether divides into two at a predetermined ratio thereby dissolving in the two layers respectively. Therefore, in the case where the reaction gas is collected with the use of the liquid compound widely used, the recovering operation of glycol ether has to be conducted with respect to both the oleaginous and aqueous layers to re-use glycol ether, and hence steps for recovery increase, thereby impairing productivity of the alkyl vinyl ether. Note that a chemical compound having an acidic hydrogen atom or a basic hydrogen atom cannot be used as the collecting agent since addition reaction occurs between alkyl vinyl ether and such compounds.

Furthermore, if distillation separation is simply conducted with respect to the collected liquid in order to purify and recover alkyl vinyl ether and glycol ether from the collected liquid, the compounds are distilled in an order from that having the lowest boiling point to that having the highest boiling point. More specifically, if the collected liquid is distilled, the following compounds are obtained in the following order: (1) acetaldehyde; (2) an azeotrope of alkyl vinyl ether and water; (3) an azeotrope of alcohol and water; (4) an azeotrope of glycol ether and water; and (5) glycol ether. Thus, if distillation separation is simply conducted, glycol ether is last obtained, and hence it takes long to conduct the distillation, thereby impairing productivity of alkyl vinyl ether. Besides, glycol ether, which is distilled together with water, cannot be recovered and re-used, since it is difficult to separate glycol ether from water. Therefore, in this case, a recovery of glycol ether decreases, and as a result, a yield and productivity of alkyl vinyl ether are further impaired.

Therefore, to establish an alkyl vinyl ether producing method suitable for industrial application, a method for efficiently collecting, purifying, and recovering alkyl vinyl ether as an object and glycol ether as non-reacted raw material from the reaction gas is earnestly demanded.

SUMMARY OF THE INVENTION

The object of the present invention is to provide a method whereby an alkyl vinyl ether is efficiently collected, purified, and recovered from a gaseous reaction mixture which is obtained by intramolecular dehydration of a glycol ether in a gas phase. Another object of the present invention is to provide a method whereby the glycol ether as non-reacted raw material of the reaction mixture is efficiently collected, purified, and recovered from the reaction mixture.

The inventors of the present application eagerly studied to provide a method for recovering an alkyl vinyl ether. As a result, it was found that an alkyl vinyl ether is efficiently collected, purified, and recovered by liquidizing and collecting a gaseous reaction mixture containing the alkyl vinyl ether by using a glycol ether, which is a raw material of the reaction mixture, as a collecting agent, the reaction mixture being obtained by intramolecular dehydration of the glycol ether in a gas phase. In addition, it was also found that by the foregoing method, the glycol ether as the raw material and the collecting agent is also efficiently collected, purified, and recovered. The present invention was completed based on these findings.

To achieve the aforementioned objects, the recovering method of alkyl vinyl ether in accordance with the present invention is characterized in comprising the step of liquidizing and collecting a gaseous reaction mixture containing an alkyl vinyl ether by using a glycol ether as a collecting agent, the glycol ether being a raw material for the alkyl vinyl ether, the reaction mixture being produced by intramolecular dehydration of the glycol ether in a gas phase.

Besides, the recovering method of alkyl vinyl ether in accordance with the present invention is characterized in that the step includes the sub-step of (a) continuously distilling collected liquid resulting on collection of the reaction mixture, by using a first distillation column, so that a distillate containing the alkyl vinyl ether and water is obtained while a bottom product containing the glycol ether are obtained.

Furthermore, the recovering method of alkyl vinyl ether in accordance with the present invention is characterized in that in the case where the bottom product of the first distillation column contains water, the step further includes the sub-step of (b) continuously distilling the bottom product together with an azeotrope former which forms an azeotrope with water, by using a second distillation column, so that a distillate containing the azeotrope is obtained while the glycol ether is obtained as a bottom product.

By the aforementioned method, alkyl vinyl ether is efficiently collected, purified, and recovered from the gaseous reaction mixture through a process having less steps than in the conventional cases. Moreover, by the foregoing method, change of properties of alkyl vinyl ether upon collection, purification, and recovery is suppressed. Furthermore, by the aforementioned method, glycol ether as the raw material of the reaction mixture and the collecting agent is efficiently collected, purified, and recovered through a process having less steps than in the conventional cases. By doing so, alkyl vinyl ether is industrially and efficiently produced.

For a fuller understanding of the nature and advantages of the invention, reference should be made to the ensuing detailed description taken in conjunction with the accompanying drawings.

DESCRIPTION OF THE PREFERRED EMBODIMENTS

In a process for recovering an alkyl vinyl ether in accordance with the present invention, the alkyl vinyl ether to be recovered is obtained by intramolecular dehydration of a glycol ether in the gas phase in the presence of a catalyst. In other words, a gaseous reaction mixture (hereinafter referred to as a reaction gas) as a target of the recovering operation is produced by intramolecular dehydration of the glycol ether in the gas phase in the presence of a catalyst.

Examples of the glycol ether are 2-methoxyethanol, 2-ethoxyethanol, 2-n-propoxyethanol, 2-isopropoxyethanol, 2-n-butoxyethanol, 2-isobutoxyethanol, 2-t-butoxyethanol, 2-amyloxyethanol, 2-hexyloxyethanol, and the like, but the glycol ether is not particularly limited. Among these compounds listed above, 2-methoxyethanol, 2-ethoxyethanol, 2-n-propoxyethanol, 2-isopropoxyethanol, 2-n-butoxyethanol, 2-isobutoxyethanol, and 2-t-butoxyethanol are particularly preferable as raw material for use in the recovery process of the present invention.

As the catalyst, though it is not particularly limited, an oxide which is expressed by the following formula is preferable:

where: M represents at least one element selected from the group consisting of alkali metal elements and alkali earth metal elements; X represents at least one element selected from the group consisting of Ti, Zr, V, Nb, Ta, Cr, Mo, W, B, Al, Ga, In, Tl, Ge, Sn, Pb, P, and Sb; and, a, b, c, and d represent a ratio of atoms, which satisfy that b is 1 to 500 and c is 0 to 1 when a is 1, and d is determined depending on values of a, b, and c, and bonding states of M, Si, X, and O.

Examples of a method for preparing a catalyst are: (1) an oxide of an element to constitute a catalyst and/or a hydroxide of the same are/is kneaded with a formation auxiliary such as water or alcohol, and after curing and drying, it is annealed; (2) a base is added to an aqueous solution of a salt and/or a halide of an element to constitute a catalyst (for example, nitrate, carbonate, carboxylate, ammonium salt, phosphate, sulfate, or the like), then, precipitate separated out is filtered, cured to form, and dried, and thereafter, it is annealed; and (3) a carrier (for example, silicagel, alumina, silicon carbide, or the like) is added to an aqueous solution of a salt and/or a halide of an element to constitute a catalyst, then, the carrier which is thus caused to carry the salt and/or the halide is dried, and thereafter, it is annealed. However, it is not particularly limited. A temperature for annealing is preferably within a range of 300° C. to 1000° C., and is more preferably within a range of 400° C. to 800° C.

Furthermore, examples of a method for preparing the catalyst expressed by the aforementioned formula are: (4) an element source containing elements represented by M and X (when necessary) (hereinafter referred to as a metal element source) and an element source containing an element represented by X (when necessary) and silicon (hereinafter referred to as a silicon source) are suspended or dissolved in water, stirred while heated so as to be condensed, then, cured to form and dried, and thereafter annealed; (5) silicon oxide already cured into a shape is solidified by heat application while being soaked in an aqueous solution of the metal element source, and thereafter it is dried, then annealed; (6) an aqueous solution of the metal element source is added to the silicon source, and it is cured to form, dried, and then, annealed; and (7) elements represented by M and X (when necessary) are doped by the ion exchange method into molecular sieves containing silicon (synthesis zeolite), then, cured to form and dried, and thereafter annealed. However, the method is not particularly limited. Such catalyst may be carried on a carrier when necessary. Examples of the metal element source are an oxide or a hydroxide of an element, a salt of an element (for example, nitrate, carbonate, carboxylate, ammonium salt, phosphate, sulfate, or the like), a halide of an element, a metal element, and the like. Examples of the silicon source are silicon oxide, silicic acid, silicate (for example, silicate of an alkali metal element or an alkali earth metal element), a molecular sieve (for example, aluminosilicate, or silicoaluminophosphate), ester of silicic acid, and the like. A temperature of annealing is preferably within a range of 300° C. to 1000° C., and is more preferably within a range of 400° C. to 800° C.

Glycol ether in the gas form is continuously brought in contact with the catalyst so that intramolecular dehydration is caused, whereby alkyl vinyl ether is produced. A type of an reactor suitable for this production is a continuous type, for example, a fixed-bed fluidization type and a fluidized-bed type, but it is not particularly limited. The catalyst may be packed in the reactor, or may be continuously supplied to the reactor.

A reaction temperature is preferably in a range of 300° C. to 600° C., and more preferably in a range of 350° C. to 500° C. A temperature lower than 300° C. is not preferable as the reaction temperature since the conversion ratio of glycol ether lowers in such a case. On the other hand, a temperature higher than 600° C. is not preferable, either, since the selectivity of alkyl vinyl ether deteriorates in such a case. A reaction pressure, that is, a pressure in the reaction system may be a normal pressure (an atmospheric pressure), or a reduced or increased pressure. A partial pressure (reaction partial pressure) of glycol ether in the gas form is adjusted to 5 mmHg to 600 mmHg by controlling the reaction pressure or by diluting glycol ether with use of a diluent, and then, glycol ether is continuously brought in contact with the catalyst. The gas hourly space velocity (GHSV) of glycol ether is preferably in a range of 1 $h^{-1}$ to 1000 $h^{-1}$, and is more preferably in a range of 10 $h^{-1}$ to 500 $h^{-1}$.

By the foregoing method, alkyl vinyl ether is continuously produced, so called, in one pot. The selectivity of alkyl vinyl ether is not less than 90 mole %. Examples of alkyl vinyl ether obtained by the aforementioned method are methyl vinyl ether, ethyl vinyl ether, n-propyl vinyl ether, isopropyl vinyl ether, n-butyl vinyl ether, isobutyl vinyl ether, t-butyl vinyl ether, amyl vinyl ether, hexyl vinyl ether, and the like, but alkyl vinyl ether is not particularly limited. Among these compounds listed above, methyl vinyl ether, ethyl vinyl ether, n-propyl vinyl ether, isopropyl vinyl ether, n-butyl vinyl ether, isobutyl vinyl ether, and t-butyl vinyl ether are particularly suitable for realizing the recovering method of the present invention.

By the aforementioned method, a reaction gas containing alkyl vinyl ether, that is, a reaction gas as a target of the recovering operation is obtained. The reaction gas contains water as a by-product, acetaldehyde and alcohol which are produced by side reaction, and non-reacted glycol ether, in addition to alkyl vinyl ether as an object. Acetaldehyde and alcohol are decomposition products which are produced when glycol ether decomposes as ether linkage dissolves. The alcohol has an alkyl group which has the same structure as that of the alkyl group of alkyl vinyl ether.

Examples of a method for continuously liquidizing and collecting the reaction gas by using as a collecting agent the glycol ether used as raw material, the examples being applicable to the recovering method of the present invention, are: (1) a method wherein the reaction gas is condensed by cooling thereby being liquidized, whereby alkyl vinyl ether and glycol ether are collected; (2) a method wherein the reaction gas is mixed with gaseous and/or liquid glycol ether, then, the mixture is condensed by cooling thereby being liquidized, whereby alkyl vinyl ether and glycol ether are collected; and (3) a method wherein the reaction gas is brought in contact with glycol ether which is jetted in a shower form or a mist form so that the reaction gas is absorbed thereto (or the reaction gas is cooled so as to be liquidized), whereby alkyl vinyl ether and glycol ether are collected. However, the method is not particularly limited. The above-listed methods may be combined when used.

In the method (1), the non-reacted glycol ether also serves as a collecting agent. Therefore, in the foregoing producing process, the conversion ratio of the glycol ether may be adjusted, that is, the reaction conditions may be adjusted, so that substantially all the reaction gas is liquidized by cooling the reaction gas to a set desired temperature. In other words, reaction of glycol ether is caused with the reaction conditions and the dew point of the obtained reaction gas adjusted depending on activity of the catalyst used, and then, the reaction gas is cooled so as to be liquidized and collected.

A quantity of the collecting agent, i.e., glycol ether, in the methods (2) and (3) may be determined depending on types of glycol ether and alkyl vinyl ether, a composition of the reaction gas (a dew point of the reaction gas), a temperature of collection, a mechanical efficiency of a collector, and the like, and it is not particularly limited. By using any one of the aforementioned methods (1) through (3), alkyl vinyl ether and glycol ether are efficiently collected.

Then, in the case where, in the aforementioned producing process, glycol ether subjected to reaction is not diluted with a diluent, that is, glycol ether with a concentration of substantially 100 percent is supplied in a gas form to the reactor so that intramolecular dehydration occurs, the efficiency in collection of alkyl vinyl ether obtained is further improved. Therefore, this is preferable from an industrial viewpoint. More specifically, since the reaction gas is not diluted with a diluent such as a non-condensable gas (for example, nitrogen gas, helium gas, and argon gas), lowering of the collection efficiency due to scattering of alkyl vinyl ether accompanying the non-condensable gas is avoided, while the quantity of the collecting agent is further decreased. Moreover, in the case where the collection temperature is kept unchanged, alkyl vinyl ether is collected at the highest concentration. This method is particularly suitable for an alkyl vinyl ether whose alkyl group has 2 to 4 carbons, namely, an alkyl vinyl ether having a relatively low boiling point and high volatility. Note that the reaction partial pressure of gaseous glycol ether with a concentration of substantially 100% may be adjusted to 5 mmHg to 600 mmHg by reducing a pressure in the reacting system.

The collected liquid obtained by collecting the reaction gas through any one of the collecting methods mentioned above is a mixture liquid containing alkyl vinyl ether, water, acetaldehyde, alcohol, glycol ether, and the like.

The following description will explain a method for continuously purifying and recovering alkyl vinyl ether and glycol ether from the collected liquid, in the recovering process in accordance with the present invention. First, an example of a distiller suitably used for recovery of alkyl vinyl ether is explained, with reference to FIGS. 1 and 2.

Figure 1:
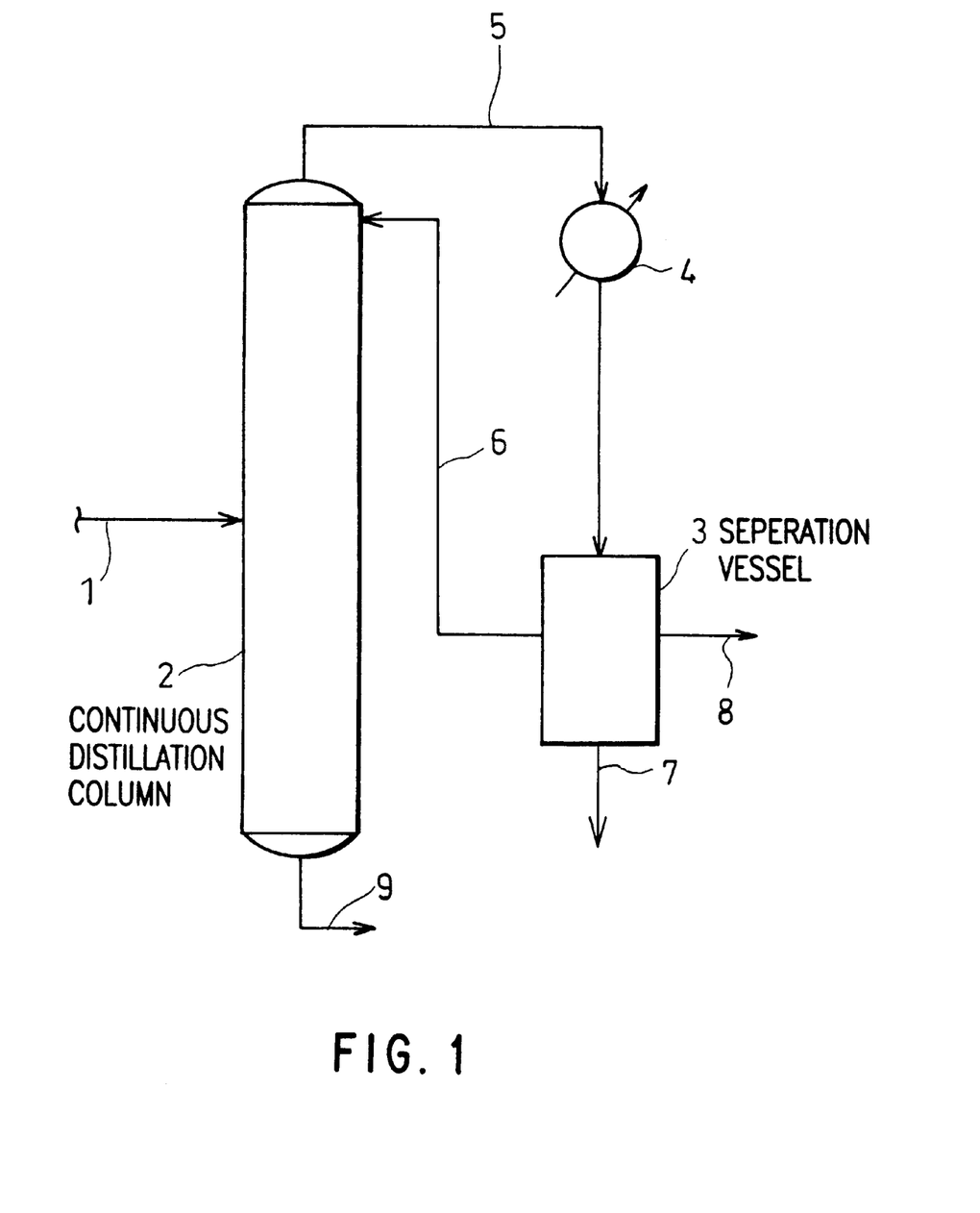
FIG. 1 is a block diagram illustrating a schematic arrangement of a continuous distillation column (first distillation column) suitably used for an alkyl vinyl ether recovering method in accordance with one embodiment of the present invention.
Figure 2:
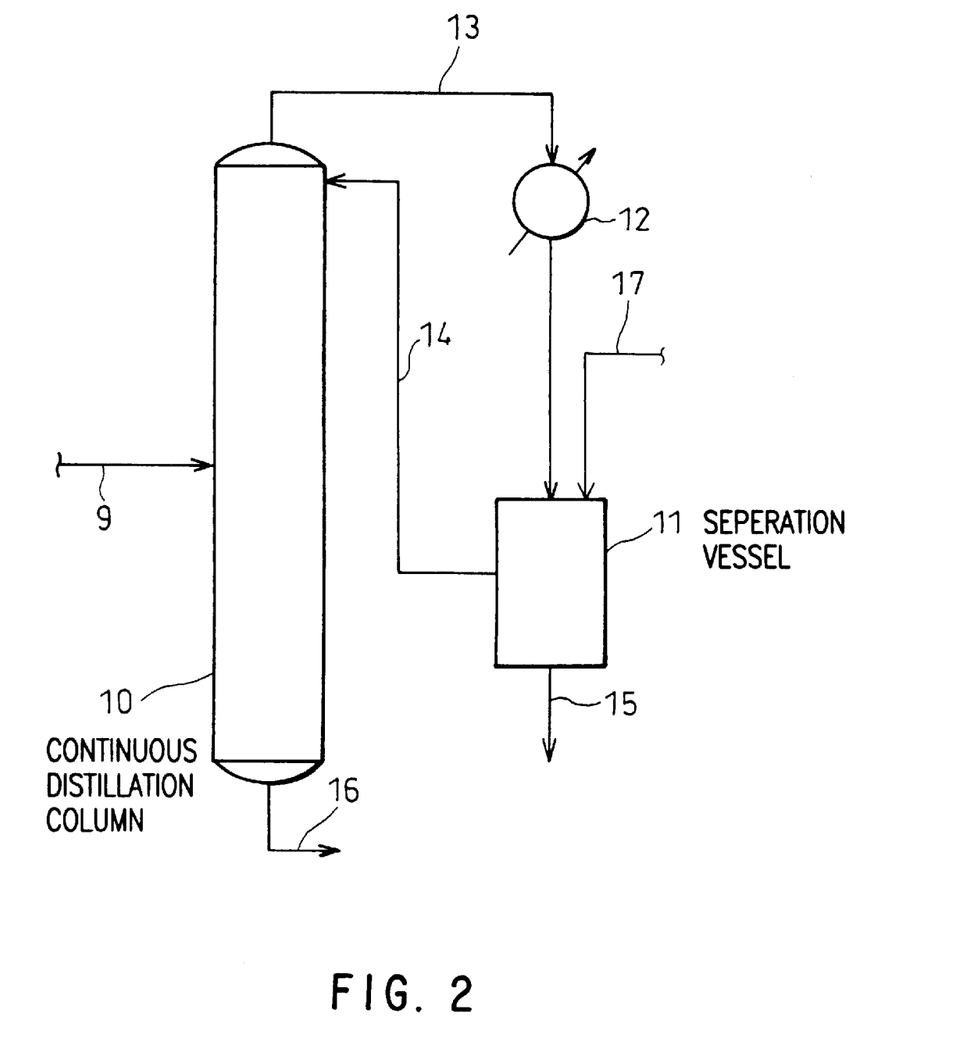
FIG. 2 is a block diagram illustrating a schematic arrangement of a continuous distillation column (second distillation column) suitably used for the alkyl vinyl ether recovery method.

As shown in FIGS. 1 and 2, the distiller is composed of a multi-stage continuous distillation column (first distillation column) 2, a separation vessel 3, a condenser 4, a multi-stage continuous distillation column (second distillation column) 10, a separation vessel 11, a condenser 12, and the like.

As shown in FIG. 1, the continuous distillation column 2 is a so-called diffusion column for diffusing alkyl vinyl ether, which continuously distills the collected liquid. A middle-stage section of the continuous distillation column 2 is connected with a collector (not shown) or a collected liquid supply device (not shown) through a pipe 1, and a column top is connected with the separation vessel 3 through a pipe 5 and the condenser 4. The continuous distillation column 2 is equipped, at the bottom thereof, with a pipe 9 through which a bottom product is continuously taken out and supplied to the continuous distillation column 10. Further, in the vicinity of the column top of the continuous distillation column 2, there is provided a pipe 6. Note that the "middle-stage section" signifies a section of stages other than the top and bottom stages in a distillation column.

The collected liquid is continuously fed to the middle-stage section in the continuous distillation column 2 through the pipe 1 from the collector or the collected liquid supply device. The continuous distillation column 2 continuously distills (diffuses) alkyl vinyl ether as well as acetaldehyde, alcohol, and water which has formed an azeotrope with alkyl vinyl ether, while it continuously produces glycol ether as the bottom product, the glycol ether containing a small quantity of alcohol, and water not always but under some operational conditions. In the vicinity of the column top of the continuous distillation column 2, a part of an oleaginous layer (described later) in the separation vessel 3 is continuously refluxed. Operational conditions of the continuous distillation column 2 are not particularly limited. An operation temperature may be set in a range such that alkyl vinyl ether and glycol ether do not have changes of properties thereof. An operation pressure may be any one of a normal pressure (an atmospheric pressure), a reduced pressure, and an increased pressure.

The condenser 4 is deposited at a predetermined desired position in the pipe 5, and it condenses (cools) and liquidizes the gas (distillate) discharged from the continuous distillation column 2.

The separation vessel 3 is a so-called decanter in which the distillate is left to stand so that the distillate separates into an oleaginous layer and an aqueous layer. The separation vessel 3 is connected with the column top of the continuous distillation column 2 through the pipe 5 and the condenser 4. Besides, at such a position in the separation vessel 3 as the oleaginous layer is extracted, pipes 6 and 8 are provided. The pipe 6 is connected with the vicinity of the column top of the continuous distillation column 2, while the pipe 8 is connected with an alkyl vinyl ether storing tank (not shown) or a fractionating column (not shown). Furthermore, at a bottom of the separation vessel 3, a pipe 7 is provided through which the aqueous layer is extracted.

The distillate of the continuous distillation column 2 is continuously fed to the separation vessel 3. The separation vessel 3 continuously supplies the oleaginous layer to the alkyl vinyl ether storing tank or the fractionating column, while it continuously refluxes a part of the oleaginous layer to the vicinity of the column top of the continuous distillation column 2. From the bottom of the separation vessel 3, the aqueous layer is appropriately taken out. Note that a compound accounting for a major part of the oleaginous layer is alkyl vinyl ether. Therefore, in the case where fractionation is substantially unnecessary, the oleaginous layer is fed to the storing tank. On the other hand, in the case where the oleaginous layer contains a trace of acetaldehyde, alcohol, or water and hence further fractionation is required, the oleaginous layer may be fractionated by a known process such as rinsing or extracting. Besides, acetaldehyde and alcohol dissolve in the aqueous layer. The aqueous layer contains substantially no alkyl vinyl ether.

As shown in FIG. 2, the continuous distillation column 10 is a so-called recovery column for recovering glycol ether, which conducts a distilling operation using an azeotrope former (described later) whereby continuously distilling a bottom product of the continuous distillation column 2. A middle-stage section of the continuous distillation column 10 is connected with a column bottom of the continuous distillation column 2 through a pipe 9, and a column top thereof is connected with the separation vessel 11 through a pipe 13 and the condenser 12. The continuous distillation column 10 is equipped, at the bottom thereof, with a pipe 16 through which a bottom product is continuously taken out. The pipe 16 is connected with a glycol ether recovery tank (not shown) or a reactor (not shown). In the vicinity of the column top of the continuous distillation column 10, there is provided a pipe 14. Note that glycol ether accounts for a major part of the bottom product of the continuous distillation column 10.

The bottom product of the continuous distillation column 2 is continuously supplied to the middle-stage section of the continuous distillation column 10 through the pipe 9. The continuous distillation column 10 continuously conducts distillation, thereby producing alcohol, water, and azeotrope former as distillate, while continuously producing glycol ether as a bottom product. In the vicinity of the column top of the continuous distillation column 10, an azeotrope former is continuously supplied (refluxed) from the separation vessel 11. Operational conditions of the continuous distillation column 10 are not particularly limited. An operation temperature may be set in such a range as the glycol ether does not have a change in properties thereof. An operation pressure may be any one of a normal pressure (an atmospheric pressure), a reduced pressure, and an increased pressure.

The condenser 12 is placed at a set desired position so as to be connected with the pipe 13, and it condenses (cools) and liquidizes the gas (distillate) taken from the continuous distillation column 10.

The separation vessel 11 is a so-called decanter in which the distillate is left to stand so that the distillate separates into an azeotrope former layer and an aqueous layer. The separation vessel 11 is connected with the column top of the continuous distillation column 10 through the pipe 13 and the condenser 12. Besides, at such a position in the separation vessel 11 as the azeotrope former layer is extracted, a pipe 14 is provided. The pipe 14 is connected with the vicinity of the column top of the continuous distillation column 10. Further, a pipe 15 is provided at the bottom of the separation vessel 11 so that the aqueous layer is taken out therethrough. Moreover, a pipe 17 for feeding the azeotrope former is provided to the separation vessel 11. The pipe 17 is connected with an azeotrope former supply tank (not shown).

The distillate from the continuous distillation column 10 is continuously supplied to the separation vessel 11. The separation vessel 11 continuously supplies (refluxes) at least a part of the azeotrope former layer to the vicinity of the column top of the continuous distillation column 10. From the bottom of the separation vessel 11, the aqueous layer is appropriately taken out. Note that alcohol dissolves in the aqueous layer. A part of the azeotrope former of some types also dissolves in the aqueous layer. Therefore, in the case where a part of the azeotrope former is taken out together with water or the like and the azeotrope former runs short in the separation vessel 11, an amount of the azeotrope former corresponding to the shortage is supplied from the azeotrope former supply tank through the pipe 17 to the separation vessel 11. By doing so, the distilling operation by the continuous distillation column 10 is further stabilized.

Note that in the distiller, there are provided various other devices necessary for the distilling operation, such as a heat exchanger, a pump, and an intermediate tank (none of them is shown), in addition to the aforementioned devices.

The foregoing azeotrope former may be any thing provided that it is an organic compound such that (1) it has a lower boiling point than that of glycol ether, (2) an azeotrope of the same and water has an azeotropic point lower than the boiling point of the azeotrope former, and (3) the azeotrope former separates from water when the azeotrope is left to stand. In the case where the boiling point of the azeotrope former is higher than that of glycol ether, an azeotropic point of an azeotrope of glycol ether and water becomes lower than that of an azeotrope of the azeotrope former and water. Therefore, glycol ether is selectively distilled, resulting in that the recovery of glycol ether lowers. Furthermore, an azeotrope former which does not separate from water is not preferable. This is because such an azeotrope former requires further separation and recovery processes for separating water and the azeotrope former so that loss of the azeotrope former is avoided, thereby causing productivity of alkyl vinyl ether to lower (causing costs to rise).

As the azeotrope former, the following are preferable: aliphatic hydrocarbon such as hexane, or heptane; alicyclic hydrocarbon such as cyclohexan; aromatic hydrocarbon such as benzene, or toluene; alkyl alcohol having four or more carbons, such as n-butanol, isobutanol, or pentanol; carboxylate such as acetate, or propionate; and ether compound such as dibutyl ether, or vinyl ether. However, the azeotrope former is not limited to these. Particularly in the case where alkyl vinyl ether to be obtained is ethyl vinyl ether, i.e., glycol ether to be recovered is 2-ethoxyethanol, alkyl alcohol having four carbons is preferably used as the azeotrope former, and among those classified as alkyl alcohol, n-butanol is particularly preferable.

The following description will explain an example of the recovering method of alkyl vinyl ether and glycol ether by using the foregoing distiller.

First of all, the collected liquid is continuously fed to the middle-stage section of the continuous distillation column 2 through the pipe 1. The collected liquid supplied to the continuous distillation column 2 is continuously subjected to a distilling operation there, whereby acetaldehyde and alcohol, as well as water as a result of azeotropic distillation, in addition to alkyl vinyl ether are taken from the column top as the distillate. Besides, glycol ether is taken from the column bottom as the bottom product, the glycol ether containing a trace of alcohol as well as water not always but under some specific operational conditions. The composition of the distillate is determined depending on the distillation conditions of the continuous distillation column 2, such as a temperature at the column top, a temperature at the column bottom, the number of stages of the column, and a quantity of the oleaginous layer refluxed from the separation vessel 3.

Here, though depending on types of alkyl vinyl ether and glycol ether, and operational conditions of the continuous distillation column 2, alkyl vinyl ether and glycol ether are continuously recovered through a single-step continuous distilling operation in the continuous distillation column 2 in the case where the oleaginous layer refluxed to the continuous distillation column 2 serves as the azeotrope former. In the case where (1) the selectivity of alkyl vinyl ether in a previous reaction is not less than 80 mole %, and (2) the continuous distillation column 2 is operated at a normal pressure (an atmospheric pressure), and further, for example, (3) glycol ether used is 2-ethoxyethanol (that is, alkyl vinyl ether is ethyl vinyl ether), a quantity of the oleaginous layer refluxed from the separation vessel 3 to the continuous distillation column 2 may be desirably controlled by setting a reflux ratio in the continuous distillation column 2 to 20 or above, or more preferably, in a range of 25 to 45. Besides, in the above case and, for example, in the case where glycol ether is 2-n-butoxyethanol (that is, alkyl vinyl ether is n-butyl vinyl ether), a quantity of the oleaginous layer refluxed from the separation vessel 3 to the continuous distillation column 2 may be desirably adjusted by setting the reflux ratio in the continuous distillation column 2 to 2.5 or above, or more preferably, in a range of 3 to 10. By doing so, glycol ether which does not contain water or alcohol is obtained as the bottom product from the column bottom without an azeotrope former, thereby enabling recovery of high-purity glycol ether. Note that a concrete method for continuously recovering alkyl vinyl ether and glycol ether through a single-step continuous distilling operation in the continuous distillation column 2 is not limited to the method wherein the reflux ratio is adjusted.

Then, the distillate from the continuous distillation column 2 is continuously supplied to the separation vessel 3. The distillate which is left to stand in the separation vessel 3 separates into the oleaginous layer and the aqueous layer. Then, by continuously or intermittently taking out the oleaginous layer from the separation vessel 3, alkyl vinyl ether is recovered. Further, a part of the oleaginous layer is continuously refluxed to the vicinity of the column top of the continuous distillation column 2, while the aqueous layer is taken from the bottom of the separation vessel 3. Thus, by refluxing a part of the oleaginous layer from the separation vessel 3 to the continuous distillation column 2, the same effect as that of a normal reflux operation is achieved at the continuous distillation column 2. Therefore, the distillate from the continuous distillation column 2 by no means contains glycol ether. Besides, since only the oleaginous layer of the distillate, with the aqueous layer excluded therefrom, is refluxed to the continuous distillation column 2, substantially no water returns to the continuous distillation column 2. In other words, by refluxing a part of the oleaginous layer from the separation vessel 3 to the vicinity of the column top of the continuous distillation column 2 through the pipe 6, the oleaginous layer is caused to function as the azeotrope former for water, thereby making removal of water from the collected liquid more efficient. Furthermore, in the case where the bottom product of the continuous distillation column 2 contains water, this means that the quantity of water to be removed by the continuous distillation column 10 decreases. Therefore, the recovery of glycol ether is more efficiently conducted in the continuous distillation column 10.

Subsequently, the bottom product of the continuous distillation column 2 is continuously supplied to the middle-stage section of the continuous distillation column 10, while the azeotrope former layer is continuously refluxed to the vicinity of the column top of the continuous distillation column 10. The bottom product supplied to the continuous distillation column 10 is continuously distilled, whereby alcohol and water are taken out together with the azeotrope from the column top, while glycol ether is taken out as the bottom product from the column bottom. Here, since at least a part of the azeotrope former layer is refluxed from the separation vessel 11 through the pipe 14 to the vicinity of the column top of the continuous distillation column 10, water is more efficiently removed. By doing so, glycol ether which is re-usable in the producing process of alkyl vinyl ether is more efficiently recovered. The composition of the bottom product is determined depending on distillation conditions at the continuous distillation column 10, for example, a temperature at the column top, a temperature at the column bottom, the number of stages in the column, and a quantity of the azeotrope former layer refluxed from the separation vessel 11.

Through the distilling operation described above, alkyl vinyl ether and glycol ether are continuously recovered from the collected liquid. Glycol ether recovered is, for example, returned to an alkyl vinyl ether producing device, so as to be re-used (recycled).

Note that with a certain composition of the collected liquid (types of alkyl vinyl ether and glycol ether), or under certain operational conditions of the continuous distillation column 2, it is possible to extract as the bottom product of the continuous distillation column 2 glycol ether containing substantially no water or impurities, that is, glycol ether which can be re-used (recycled) in the producing process of alkyl vinyl ether. Besides, under certain operational conditions of the continuous distillation column 2, it is possible to extract alkyl vinyl ether from the distillate of the continuous distillation column 2, while obtain as the bottom product glycol ether containing substantially no water or impurities. In other words, through a single-step distilling operation, alkyl vinyl ether is diffused and recovered, while glycol ether is efficiently recovered at high purity.

As described above, by the recovering method of the present invention, alkyl vinyl ether is efficiently collected, purified, and recovered from the reaction gas, while glycol ether as the raw material and the collecting agent is efficiently collected, purified, and recovered. In other words, by the recovering method of the present invention, it is possible to industrially and effectively produce alkyl vinyl ether.

Figure 3:
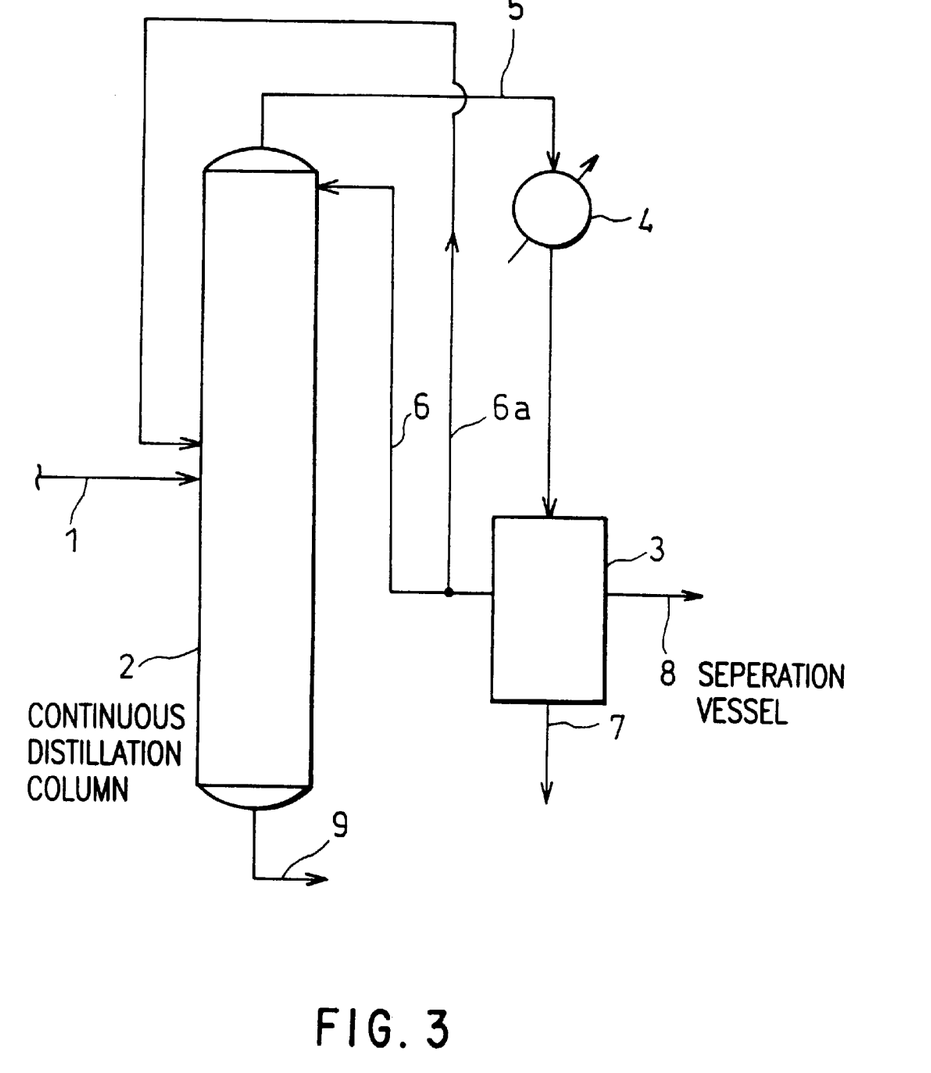
FIG. 3 is a block diagram illustrating a variation of the continuous distillation column shown in FIG. 1.

In the above description, a case where a part of the oleaginous layer in the separation vessel 3 is continuously supplied (refluxed) to the vicinity of the column top of the continuous distillation column 2 through the pipe 6 is described, but a place to which the oleaginous layer is supplied is not particularly limited. For example, as shown in FIG. 3, it may be arranged as follows. Namely, a branch pipe 6a which diverges from the pipe 6 may be connected with the middle-stage section of the continuous distillation column 2, or more specifically, a certain stage between a stage connected with the pipe 1 and a stage connected with the pipe 6 in the continuous distillation column 2, whereby at least a part of the oleaginous layer of the separation vessel 3 is supplied through the pipe 6 and the branch pipe 6a to the vicinity of the column top and the middle-stage section of the continuous distillation column 2, respectively.

Figure 4:
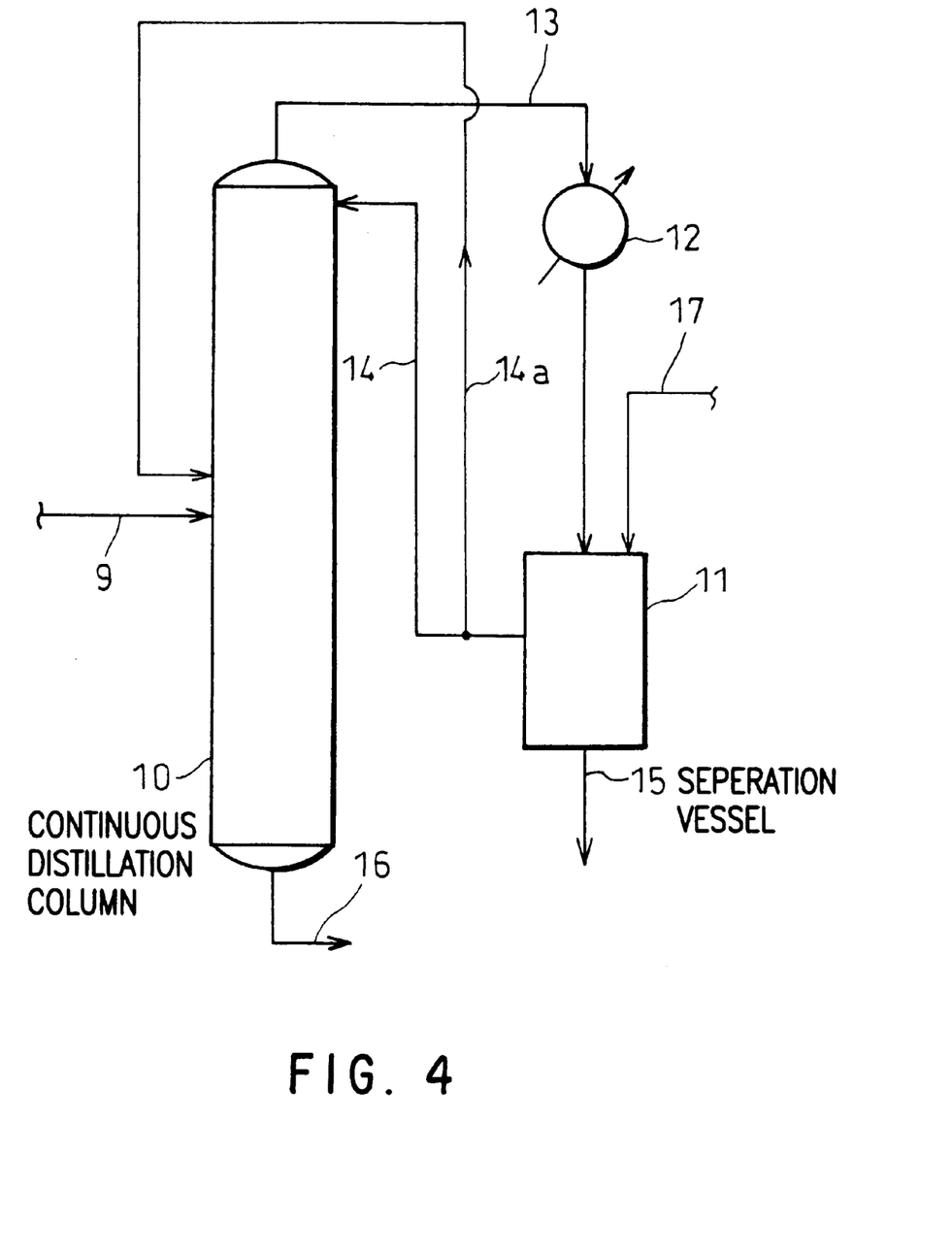
FIG. 4 is a block diagram illustrating a variation of the continuous distillation column shown in FIG. 2.

Furthermore, in the aforementioned description, a case where at least a part of the azeotrope former layer in the separation vessel 11 is supplied (refluxed) through the pipe 14 to the vicinity of the column top of the continuous distillation column 10 is described, but a place where the azeotrope former layer is supplied is not particularly limited. For example, as shown in FIG. 4, it may be arranged as follows. Namely, a branch pipe 14a which diverges from the pipe 14 may be connected with the middle-stage section of the continuous distillation column 10, that is, a certain stage between a stage connected with the pipe 9 and a stage connected with the pipe 14 in the continuous distillation column 10, whereby a part of the azeotrope former layer of the separation vessel 11 is supplied through the pipe 14 and the branch pipe 14a to the vicinity of the column top and the middle-stage section of the continuous distillation column 10, respectively. Furthermore, an arrangement of the distiller is not limited to that shown in FIGS. 1 through 4.

The alkyl vinyl ether recovering method of the present invention is, as described above, a method wherein a reaction gas (a gaseous reaction mixture) which is generated by intramolecular dehydration of glycol ether in the gas phase and contains alkyl vinyl ether is liquidized and collected with use of glycol ether as a collecting agent, which is a raw material of the reaction gas. The method is also characterized in that the reaction gas is generated by causing intramolecular dehydration to glycol ether with a concentration of substantially 100% in the gas phase.

The alkyl vinyl ether recovering method of the present invention is characterized in that a collected liquid resulting on collection of the reaction gas is continuously distilled by a first distillation column so that a distillate containing alkyl vinyl ether and water is obtained, while a bottom product containing glycol ether is obtained. Besides, by leaving the distillate from the first distillation column to stand, the distillate is caused to separate into an oleaginous layer and an aqueous layer. Furthermore, a part of the oleaginous layer is refluxed to the column top of the first distillation column.

Moreover, the alkyl vinyl ether recovering method of the present invention is a method wherein, in the case where the bottom product of the first distillation column contains water, the bottom product is continuously distilled by a second distillation column together with an azeotrope former which forms an azeotrope with water, whereby a distillate containing the azeotrope is obtained while glycol ether is obtained as a bottom product. Besides, the method is characterized in that the distillate from the second distillation column is left to stand, so that it separates into an azeotrope former layer and an aqueous layer. Furthermore, the method is characterized in that a part of the azeotrope former layer is refluxed to the column top of the second distillation column.

By the foregoing method, alkyl vinyl ether is efficiently collected, purified, and recovered through less steps than in the conventional cases. Besides, by the aforementioned method, a change of properties of alkyl vinyl ether during collection, purification, and recovery can be suppressed. Moreover, by the aforementioned method, glycol ether which is the raw material and the collecting agent is efficiently collected, purified and recovered form the reaction gas through less steps than in the conventional cases. By doing so, alkyl vinyl ether is industrially and efficiently produced.

The following description will more concretely explain the present invention by showing examples, but the present invention is not limited by these examples. Note that a conversion ratio of glycol ether, and a selectivity, a once-through yield, and a collection ratio of alkyl vinyl ether are defined as follows:

$$\text{CONVERSION RATIO OF GLYCOL ETHER (mole \%)} = \frac{\text{THE MOLAR NUMBER OF CONSUMED GLYCOL ETHER}}{\text{THE MOLAR NUMBER OF GLYCOL ETHER SUPPLIED TO REACTOR}} \times 100$$

$$\text{SELECTIVITY OF ALKYL VINYL ETHER (mole \%)} = \frac{\text{THE MOLAR NUMBER OF PRODUCED ALKYL VINYL ETHER}}{\text{THE MOLAR NUMBER OF CONSUMED GLYCOL ETHER}} \times 100$$

$$\text{ONCE-THROUGH YIELD OF ALKYL VINYL ETHER (mole \%)} = \frac{\text{THE MOLAR NUMBER OF PRODUCED ALKYL VINYL ETHER}}{\text{THE MOLAR NUMBER OF GLYCOL ETHER SUPPLIED TO REACTOR}} \times 100$$

COLLECTION RATIO OF ALKYL VINYL ETHER (mole %) =

-continued $$\frac{\text{THE MOLAR NUMBER OF COLLECTED ALKYL VINYL ETHER}}{\text{THE MOLAR NUMBER OF PRODUCED ALKYL VINYL ETHER}} \times 100$$

EXAMPLE 1

A catalyst necessary for producing alkyl vinyl ether was prepared. More specifically, 300 g of silicon oxide was added to an aqueous solution obtained by dissolving 25 g of cesium hydroxide in 1,000 g of water, and then, the mixture was heated and mixed by hot-water bathing so as to be concentrated (solidified and dried). The resultant powdery substance was formed to a spherical pellet with a diameter of about 5 mm. Subsequently, the pellet thus obtained was fully dried in an air atmosphere at a temperature of 120° C., and then, it was annealed in an air atmosphere at a temperature of 500° C. for 2 hours. A ratio of atoms composing the catalyst excluding oxygen was $Cs_1Si_{30}$. By using this catalyst, an alkyl vinyl ether was produced.

A device used as a reactor was a reaction tube made of stainless steal with an inside diameter of 30 mm to which a vacuum pump was connected. Additionally, a cooler with an outer casing as a collector was connected with an outlet of the reaction tube, while a receiving unit was connected with the cooler. After packing the foregoing catalyst 1 L in the reaction tube, an internal temperature of the reaction tube was raised to 370° C., and an internal pressure of the reaction tube was lowered while the temperature was maintained. Subsequently, the pressure (reaction pressure) of the catalyst layer at the outlet was adjusted to 230 mmHg, while 2-ethoxyethanol as a glycol ether was continuously supplied at a gas hourly space velocity of 100 h$^{-1}$ (supplied quantity: 402 g/hr), so that reaction occurred. Meanwhile, internal pressures of the cooler and the receiving unit were also adjusted to 230 mmHg.

A reaction gas obtained (a reaction mixture) was analyzed by using a gas chromatography (GC). As a result, the conversion ratio of 2-ethoxyethanol, the selectivity of ethyl vinyl ether as an alkyl vinyl ether, and the once-through yield thereof were found to be 21.4 mole %, 92.5 mole %, and 19.8 mole %, respectively. Subsequently, the reaction gas was collected. More specifically, a refrigerant cooled to −5° C. to 0° C. was run through the outer casing, while the reaction gas was run through the cooler, whereby the reaction gas was cooled and condensed, thereby becoming liquidized. The resultant liquid was collected in the receiving unit which was cooled to 5° C., whereby a collected liquid was obtained.

The collected liquid was analyzed by using the gas chromatography. The result showed that the collected liquid contained ethyl vinyl ether at a ratio such that the yield thereof was 19.6 mole % with respect to the supplied 2-ethoxyethanol. Therefore, a collection ratio of ethyl vinyl ether was 99.0 mole %.

EXAMPLE 2

The same reaction and operation as those in Example 1 were conducted, except that the reaction pressure, which was 230 mmHg in Example 1, was set to 500 mmHg. As a result, the conversion ratio of 2-ethoxyethanol, the selectivity of ethyl vinyl ether as an alkyl vinyl ether, the once-through yield thereof, and the collection ratio thereof were 20.4 mole %, 90.8 mole %, 18.5 mole %, and 99.5 mole %, respectively.

EXAMPLE 3

The same reaction and operation as those in Example 1 were conducted except that in lieu of 2-ethoxyethanol in Example 1, 2-n-butoxyethanol was used as a glycol ether and the reaction pressure, which was 230 mmHg in Example 1, was set to 70 mmHg. As a result, the conversion ratio of 2-n-butoxyethanol, the selectivity of n-butyl vinyl ether as an alkyl vinyl ether, the once-through yield thereof, and the collection ratio thereof were 28.8 mole %, 93.6 mole %, 27.0 mole %, and 99.3 mole %, respectively.

EXAMPLE 4

As a reactor, a reaction tube made of stainless steal with an inside diameter of 30 mm to which a vacuum pump was connected was used. Additionally, a cooler with an outer casing as a collector was connected with an outlet of the reaction tube, while a receiving unit was connected with the cooler. Further, an introducing pipe for introducing a collecting agent was provided at a set desired position between the outlet of the reaction tube and the cooler. After packing in the reaction tube a catalyst 1 L which was prepared through the same operation as that in Example 1, the internal temperature of the reaction tube was raised to 370° C., and the internal pressure of the reaction tube was lowered while the temperature was maintained. Subsequently, the pressure (reaction pressure) of the catalyst layer at the outlet was adjusted to 230 mmHg, while 2-ethoxyethanol was continuously supplied thereto at a gas hourly space velocity of 40 h$^{-1}$ (supplied quantity: 161 g/hr), so that reaction occurred. Meanwhile, internal pressures of the cooler and the receiving unit were also adjusted to 230 mmHg.

A reaction gas obtained was analyzed by using a gas chromatography. As a result, the conversion ratio of 2-ethoxyethanol, the selectivity of ethyl vinyl ether, and the once-through yield thereof were found to be 48.9 mole %, 91.8 mole %, and 44.9 mole %, respectively. Subsequently, the reaction gas was collected. More specifically, a refrigerant cooled to −5° C. to 0° C. was run through the outer casing, while the reaction gas was run through the cooler. Further, 2-ethoxyethanol as the collecting agent was continuously added to the reaction gas through the introducing pipe at a rate of 300 g/hr. By doing so, the reaction gas was cooled and condensed, thereby being liquidized. The resultant liquid was collected in the receiving unit which was cooled to 5° C., whereby a collected liquid was obtained.

The collected liquid was analyzed by using the gas chromatography. The result showed that the collected liquid contained ethyl vinyl ether at a ratio such that a yield thereof was 43.8 mole % with respect to 2-ethoxyethanol supplied to the reactor. Therefore, the collection ratio of ethyl vinyl ether was 97.6 mole %.

EXAMPLE 5

A catalyst necessary for producing an alkyl vinyl ether was prepared. More specifically, 300 g of silicon oxide was added to an aqueous solution obtained by dissolving 97.5 g of cesium nitrate and 52.8 g of secondary ammonium phosphate in 1,000 g of water, and then, the mixture was heated and mixed by hot-water bathing so as to be concentrated (solidified and dried). The resultant powdery substance was formed to a spherical pellet with a diameter of about 5 mm. Subsequently, the pellet thus obtained was fully dried in an air atmosphere at a temperature of 120° C., and then, it was annealed in an air atmosphere at a temperature of 600° C. for 2 hours. A ratio of atoms composing the catalyst excluding oxygen was $Cs_1Si_{10}P_{0.8}$. By using this catalyst, an alkyl vinyl ether was produced.

As a reactor, a reaction tube made of stainless steal with an inside diameter of 30 mm to which a vacuum pump was connected was used. Additionally, a cooler with an outer casing as a collector was connected with an outlet of the reaction tube, while a receiving unit was connected with the cooler. After packing the foregoing catalyst 1 L in the reaction tube, the internal temperature of the reaction tube was raised to 450° C., and the internal pressure of the reaction tube was lowered while the temperature was maintained. Subsequently, the pressure (reaction pressure) of the catalyst layer at the outlet was adjusted to 380 mmHg, while 2-isopropoxyethanol as a glycol ether was continuously supplied at a gas hourly space velocity of 150 h$^{-1}$ (supplied quantity: 697 g/hr), so that reaction occurred. Meanwhile, internal pressures of the cooler and the receiving unit were also adjusted to 380 mmHg.

A reaction gas obtained was analyzed by using a gas chromatography. As a result, the conversion ratio of 2-isopropoxyethanol, the selectivity of isopropyl vinyl ether as an alkyl vinyl ether, and the once-through yield thereof were found to be 25.3 mole %, 93.3 mole %, and 23.6 mole %, respectively. Subsequently, the reaction gas was collected. More specifically, a refrigerant cooled to −5° C. to 0° C. was run through the outer casing, while the reaction gas was run through the cooler, whereby the reaction gas was cooled and condensed, thereby becoming liquidized. The resultant liquid was collected in the receiving unit which was cooled to 5° C., whereby a collected liquid was obtained.

The collected liquid was analyzed by using the gas chromatography. The result showed that the collected liquid contained isopropyl vinyl ether at a ratio such that a yield thereof was 23.4 mole % with respect to the supplied 2-isopropoxyethanol. Therefore, the collection ratio of ethyl vinyl ether was 99.2 mole %.

EXAMPLE 6

A catalyst necessary for producing an alkyl vinyl ether was prepared. More specifically, an aqueous solution obtained by dissolving 73.8 g of rubidium nitrate in 1,000 g of water was heated to 90° C. Then, 300 g of silicon oxide was added thereto, and the mixture was heated and stirred so as to be concentrated (solidified and dried). The resultant powdery substance was formed to a spherical pellet with a diameter of about 5 mm. Subsequently, the pellet thus obtained was fully dried in an air atmosphere at a temperature of 120° C., and then, it was annealed in an air atmosphere at a temperature of 500° C. for 2 hours. A ratio of atoms composing the catalyst excluding oxygen was $Rb_1Si_{10}$. By using this catalyst, an alkyl vinyl ether was produced.

As a reactor, a reaction tube made of stainless steal with an inside diameter of 30 mm to which a vacuum pump was connected was used. Additionally, a cooler with an outer casing as a collector was connected with an outlet of the reaction tube, while a receiving unit was connected with the cooler. Further, an introducing pipe for introducing a collecting agent was provided at a set desired position between the outlet of the reaction tube and the cooler. After packing the foregoing catalyst 1 L in the reaction tube, the internal temperature of the reaction tube was raised to 440° C., and the internal pressure of the reaction tube was lowered while the temperature was maintained. Subsequently, the pressure of the catalyst layer at the outlet was adjusted to 200 mmHg, while 2-ethoxyethanol was continuously supplied at a gas hourly space velocity of 75 h$^{-1}$ (supplied quantity: 302 g/hr), so that reaction occurred. Meanwhile, internal pressures of the cooler and the receiving unit were also adjusted to 200 mmHg.

A reaction gas obtained was analyzed by using a gas chromatography. As a result, the conversion ratio of 2-ethoxyethanol, the selectivity of ethyl vinyl ether, and the once-through yield thereof was found to be 75.1 mole %, 87.8 mole %, and 65.9 mole %, respectively. Subsequently, the reaction gas was collected. More specifically, a refrigerant cooled to −5° C. to 0° C. was run through the outer casing, while the reaction gas was run through the cooler. Further, 2-ethoxyethanol as the collecting agent was continuously added to the reaction gas through the introducing pipe at a rate of 2,000 g/hr. The resultant liquid was collected in the receiving unit which was cooled to 5° C., whereby a collected liquid was obtained.

The collected liquid was analyzed by using the gas chromatography. The result showed that the collected liquid contained ethyl vinyl ether at a ratio such that a yield thereof was 63.1 mole % with respect to the supplied 2-ethoxyethanol. Therefore, the collection ratio of ethyl vinyl ether was 95.8 mole %.

EXAMPLE 7

By using the distiller shown in FIGS. 1 and 2, ethyl vinyl ether as an object and 2-ethoxyethanol as a non-reacted raw material were continuously collected from the collected liquid obtained in Example 1. As the continuous distillation columns 2 and 10, oldershaw distillation columns were used, which had an inside diameter of 30 mm, 10 stages in a condensing section, and 10 stages in a recovering section each. The inner temperature of the separation vessels 3 and 11, i.e., a temperature of the distillate to be left to stand was kept at 10° C. As an azeotrope former, n-butanol was used.

Then, the continuous distillation columns 2 and 10 were operated at a normal pressure. Here, a quantity of the oleaginous layer refluxed from the separation vessel 3 to the continuous distillation column 2 was adjusted so that a reflux ratio at the continuous distillation column 2 became 5. Further, a quantity of the azeotrope former layer to be refluxed from the separation vessel 11 to the continuous distillation column 10 was adjusted so that a reflux ratio at the continuous distillation column 10 became 10.

Regarding each composition, a quantity per unit time (hereinafter referred to as a supply rate) of the collected liquid supplied to the continuous distillation column 2, a quantity per unit time (hereinafter referred to as a distillation rate) of the distillate taken from the continuous distillation column 2, a quantity per unit time (hereinafter referred to as a bottom product rate) of the bottom product taken from the continuous distillation column 2, a supply rate of the bottom product to the continuous distillation column 10, a distillation rate of the distillate taken from the continuous distillation column 10, and a bottom product rate of the bottom product taken from the distillation column 10 are shown in Table 1 below. Note that in the table, descriptions on the rate and composition regarding the azeotrope former in the continuous distillation column 10 are omitted.

TABLE 1

| | COMPOSITION (g/hr) | | | | | |
|---|---|---|---|---|---|---|
| | ETHYL VINYL ETHER | 2-ETHOXY-ETHANOL | ACET-ALDEHYDE | ETHANOL | WATER | OTHERS |
| CONTINUOUS DISTILLATION COLUMN 2 | | | | | | |
| SUPPLY RATE | 133.6 | 669.5 | 6.2 | 7.0 | 33.7 | 0 |
| DISTILLATION RATE | 132.5 | 0 | 5.1 | 5.6 | 4.3 | 0 |
| BOTTOM PRODUCT RATE | 0 | 668.4 | 0 | 1.4 | 29.4 | 2.5 |
| CONTINUOUS DISTILLATION COLUMN 10 | | | | | | |
| SUPPLY RATE | 0 | 668.4 | 0 | 1.4 | 29.4 | 2.5 |
| DISTILLATION RATE | 0 | 1.6 | 0 | 1.4 | 29.4 | 1.0 |
| BOTTOM PRODUCT RATE | 0 | 666.8 | 0 | 0 | 0 | 1.5 |

As clear from the figures shown in Table 1, in the continuous distillation column 2, all ethyl vinyl ether was taken out together with acetaldehyde, ethanol and water as distillate, while all 2-ethoxyethanol was taken out together with the rest of water as a bottom product. In respect to the continuous distillation column 10, it is clear that all water in the bottom product was taken out together with the azeotrope former and others as a distillate, while 2-ethoxyethanol was taken out as a bottom product. Accordingly, the table shows that by using the foregoing distiller, that is, by the recovering method of the present invention, ethyl vinyl ether and 2-ethoxyethanol are continuously recovered.

A ratio of the quantity of ethyl vinyl ether distilled by the continuous distillation column 2 with respect to the quantity of ethyl vinyl ether which was contained in the collected liquid supplied to the continuous distillation column 2, that is, the recovery rate of ethyl vinyl ether, was 99.2 weight percent (wt. %).

On the other hand, a ratio of the quantity of 2-ethoxyethanol taken from the continuous distillation column 10 with respect to the quantity of 2-ethoxyethanol which was contained in the collected liquid supplied to the continuous distillation column 2, that is, the recovery rate of 2-ethoxyethanol, was 99.6 wt. %. 2-ethoxyethanol recovered had a purity of 99.7 wt. %.

Major impurities contained in 2-ethoxyethanol recovered (indicated as "others" in the table) were high-boiling-point substances resulting on transformation of a small part of ethyl vinyl ether or 2-ethoxyethanol due to some causes during the distilling operation, and n-butanol as the azeotrope former. The reason why acetaldehyde decreased during the distilling operation is considered that since acetaldehyde has a low boiling point, a part of the same was scattered out of the distillation system.

EXAMPLE 8

By using the distiller shown in FIGS. 1 and 2, isopropyl vinyl ether as an object and 2-isopropoxyethanol as a non-reacted raw material were continuously collected from the collected liquid obtained in Example 5. As the continuous distillation columns 2 and 10, oldershaw distillation columns of the same type as those used in Example 7 were used. The inner temperature of the separation vessels 3 and 11, that is a temperature of the distillate to be left to stand was kept at 10° C. As an azeotrope former, n-butanol was used. The continuous distillation columns 2 and 10 were operated under the same conditions as those in Example 7.

Regarding each composition, a supply rate of the collected liquid supplied to the continuous distillation column 2, a distillation rate of the distillate taken from the continuous distillation column 2, a bottom product rate of the bottom product taken from the continuous distillation column 2, a supply rate of the bottom product to the continuous distillation column 10, a distillation rate of the distillate from the continuous distillation column 10, and a bottom product rate of the bottom product from the distillation column 10 are shown in Table 2 below. Note that in the table, descriptions on the rate and composition regarding the azeotrope former in the continuous distillation column 10 are omitted.

TABLE 2

| | COMPOSITION (g/hr) | | | | | |
|---|---|---|---|---|---|---|
| | ISOPROPYL VINYL ETHER | 2-ISOPROPOXY-ETHANOL | ACET-ALDEHYDE | ISO-PROPANOL | WATER | OTHERS |
| CONTINUOUS DISTILLATION COLUMN 2 | | | | | | |
| SUPPLY RATE | 161.1 | 621.5 | 5.9 | 7.7 | 34.0 | 0.4 |
| DISTILLATION RATE | 159.5 | 0 | 4.6 | 6.6 | 22.4 | 0.3 |
| BOTTOM | 0 | 621.1 | 0 | 1.1 | 11.6 | 2.1 |

TABLE 2-continued

| | COMPOSITION (g/hr) | | | | | |
|---|---|---|---|---|---|---|
| | ISOPROPYL VINYL ETHER | 2-ISOPROPOXY-ETHANOL | ACET-ALDEHYDE | ISO-PROPANOL | WATER | OTHERS |
| PRODUCT RATE CONTINUOUS DISTILLATION COLUMN 10 | | | | | | |
| SUPPLY RATE | 0 | 621.1 | 0 | 1.1 | 11.6 | 2.1 |
| DISTILLATION RATE | 01.8 | 0 | 1.1 | 11.6 | 0 | |
| BOTTOM PRODUCT RATE | 0 | 619.3 | 0 | 0 | 0 | 2.1 |

As clear from the figures shown in Table 2, in the continuous distillation column 2, all isopropyl vinyl ether was taken out together with acetaldehyde, isopropanol and water as distillate, while all 2-isopropoxyethanol was taken out with the rest of water as a bottom product. In respect to the continuous distillation column 10, it is clear that all water in the bottom product was taken out together with the azeotrope former and others as a distillate, while 2-isopropoxyethanol was taken out as a bottom product. Accordingly, the table shows that by using the foregoing distiller, that is, by the recovering method of the present invention, isopropyl vinyl ether and 2-isopropoxyethanol are continuously recovered.

A ratio of the quantity of isopropyl vinyl ether distilled by the continuous distillation column 2 with respect to the quantity of isopropyl vinyl ether that was contained in the collected liquid supplied to the continuous distillation column 2, that is, the recovery rate of isopropyl vinyl ether, was 99.0 wt. %.

On the other hand, a ratio of the quantity of isopropoxy-ethanol taken from the continuous distillation column 10 with respect to the quantity of 2-isopropoxyethanol that was contained in the collected liquid supplied to the continuous distillation column 2, that is, the recovery rate of 2-isopropoxyethanol, was 99.6 wt. %. 2-isopropoxyethanol recovered had a purity of 99.7 wt. %.

Major impurities contained in 2-ethoxyethanol recovered were high-boiling-point substances resulting on transformation of a small part of isopropyl vinyl ether or 2-isopropoxyethanol due to some causes during the distilling operation, and n-butanol as the azeotrope former. The reason why acetaldehyde decreased during the distilling operation is considered that since acetaldehyde has a low boiling point, a part of the same was scattered out of the distillation system.

EXAMPLE 9

By using the distiller shown in FIG. 1, ethyl vinyl ether as an object and 2-ethoxyethanol as a non-reacted raw material were continuously collected from the collected liquid obtained in Example 1. As the continuous distillation column 2, an oldershaw distillation column having an inside diameter of 50 mm, 10 stages in the condensing section, and 10 stages in the recovering section was used. The inner temperature of the separation vessel 3, that is a temperature of the distillate to be left to stand was kept at 10° C.

Then, the continuous distillation column 2 was operated at a normal pressure. Here, a quantity of the oleaginous layer refluxed from the separation vessel 3 to the continuous distillation column 2 was adjusted so that a reflux ratio at the continuous distillation column 2 became 40. Under the above operational conditions, the oleaginous layer refluxed to the continuous distillation column 2 functioned as the azeotrope former as well.

Regarding each composition, a supply rate of the collected liquid supplied to the continuous distillation column 2, a distillation rate of the distillate taken from the continuous distillation column 2, and a bottom product rate of the bottom product taken from the continuous distillation column 2 are shown in Table 3 below.

TABLE 3

| | COMPOSITION (g/hr) | | | | | |
|---|---|---|---|---|---|---|
| | ETHYL VINYL ETHER | 2-ETHOXY-ETHANOL | ACET-ALDEHYDE | ETHANOL | WATER | OTHERS |
| CONTINUOUS DISTILLATION COLUMN 2 | | | | | | |
| SUPPLY RATE | 133.6 | 669.5 | 6.2 | 7.0 | 33.7 | 0 |
| DISTILLATION RATE | 130.3 | 1.6 | 5.4 | 8.1 | 33.1 | 0.2 |
| BOTTOM PRODUCT RATE | 0 | 665.4 | 0 | 0 | 0 | 4.4 |

As clear from the figures shown in Table 3, in the continuous distillation column 2, all ethyl vinyl ether was taken out with all acetaldehyde, ethanol and water as distillate, while all 2-ethoxyethanol was taken out as a high-purity bottom product. Accordingly, the table shows that by using the foregoing distiller, that is, by the recovering method of the present invention, ethyl vinyl ether and 2-ethoxyethanol are continuously recovered.

To be more specific, though a reflux ratio at the continuous distillation column 2 increases, there is no need to prepare an azeotrope former in particular, since under the above operational conditions, the oleaginous layer refluxed to the continuous distillation column 2 functions as an azeotrope former as well. Therefore, 2-n-ethoxyethanol can be recovered by the single-step continuous distilling operation at the continuous distillation column 2.

The recovery rate of ethyl vinyl ether was 97.5 wt. %. On the other hand, the recovery rate of 2-ethoxyethanol was 99.4 wt. %. 2-ethoxyethanol recovered had a purity of 99.3 wt. %. Major impurities contained in 2-ethoxyethanol recovered were high-boiling-point substances resulting on transformation of a small part of ethyl vinyl ether or 2-ethoxyethanol due to some causes during the distilling operation.

EXAMPLE 10

By using the distiller shown in FIG. 1, n-butyl vinyl ether as an object and 2-n-butoxyethanol as a non-reacted raw material were continuously collected from the collected liquid obtained in Example 3. As the continuous distillation column 2, an oldershaw distillation column having an inside diameter of 30 mm, 10 stages in the condensing section, and 10 stages in the recovering section was used. The inner temperature of the separation vessel 3, that is a temperature of the distillate to be left to stand was kept at 10° C.

Then, the continuous distillation column 2 was operated at a normal pressure. Here, a quantity of the oleaginous layer refluxed from the separation vessel 3 to the continuous distillation column 2 was adjusted so that a reflux ratio at the continuous distillation column 2 became 7. Under the above operational conditions, the oleaginous layer refluxed to the continuous distillation column 2 functioned as the azeotrope former as well.

Regarding each composition, a supply rate of the collected liquid supplied to the continuous distillation column 2, a distillation rate of the distillate taken from the continuous distillation column 2, and a bottom product rate of the bottom product taken from the continuous distillation column 2 are shown in Table 4 below.

butoxyethanol can be recovered by the single-step continuous distilling operation at the continuous distillation column 2.

The recovery rate of n-butyl vinyl ether was 99.6 weight percent (wt. %). On the other hand, the recovery rate of 2-n-butoxyethanol was 99.8 wt. %. 2-n-butoxyethanol recovered had a purity of 99.7 wt. %. Major impurities contained in 2-n-butoxyethanol recovered were high-boiling-point substances resulting on transformation of a small part of n-butyl vinyl ether or 2-n-butoxyethanol due to some causes during the distilling operation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of recovering alkyl vinyl ether from a gaseous reaction mixture containing a alkyl vinyl ether, the gaseous reaction mixture being produced by intramolecular dehydration of a glycol ether as a raw material in a gas phase, the method comprising:

adding a supplemental amount of said glycol ether to at least one of the raw material and the gaseous reaction mixture such that the supplemental amount of said glycol ether functions as a collecting agent; and liquidizing the gaseous reaction mixture to collect the alkyl vinyl ether and said glycol ether.

2. The method according to claim 1, wherein the gaseous reaction mixture is produced by causing intramolecular dehydration to the glycol ether with a concentration of substantially 100 percent in the gas phase.

3. The method according to claim 1, wherein said step of liquidizing includes:

cooling the gaseous reaction mixture for condensing and liquidizing same.

4. The method according to claim 1, wherein:

said step of adding includes mixing the glycol ether in at least one of a gas form and a liquid form with the gaseous reaction mixture; and

TABLE 4

| | COMPOSITION (g/hr) | | | | | |
|---|---|---|---|---|---|---|
| | BUTYL VINYL ETHER | 2-BUTOXY-ETHANOL | ACET-ALDEHYDE | n-BUTANOL | WATER | OTHERS |
| CONTINUOUS DISTILLATION COLUMN 2 | | | | | | |
| SUPPLY RATE | 161.2 | 504.8 | 4.5 | 8.2 | 29.2 | 0 |
| DISTILLATION RATE | 160.6 | 0 | 4.3 | 8.3 | 29.1 | 0 |
| BOTTOM PRODUCT RATE | 0 | 503.8 | 0 | 0 | 0 | 1.6 |

As clear from the figures shown in Table 4, in the continuous distillation column 2, all butyl vinyl ether was taken out with all acetaldehyde, butanol and water as distillate, while all 2-n-butoxyethanol was taken out as a high-purity bottom product. Accordingly, the table shows that by using the foregoing distiller, that is, by the recovering method of the present invention, n-butyl vinyl ether and 2-n-butoxyethanol are continuously recovered.

To be more specific, since under the above operational conditions, the oleaginous layer refluxed to the continuous distillation column 2 functions as an azeotrope former as well, there is no need to prepare an azeotrope former in particular. Therefore, n-butyl vinyl ether and 2-n- said step of liquidizing includes cooling the gaseous reaction mixture for condensing and liquidizing same.

5. The method of according to claim 1, wherein said step of adding includes:

bringing the reaction mixture in contact with the glycol ether jetted in one of a shower form and a mist form so that the gaseous reaction mixture is absorbed therein.

6. The method according to claim 1, wherein:

said step of adding includes bringing the gaseous reaction mixture in contact with the glycol ether jetted in one of a shower form and a mist form; and said step of liquidizing includes cooling the gaseous reaction mixture.

7. The method according to claim 1, further comprising:

continuously distilling collected liquid resulting on collection of the reaction mixture, by using a first distillation column, so that a distillate containing the alkyl vinyl ether and water is obtained, while a bottom product containing the glycol ether is obtained.

8. The method according to claim 7, wherein said step of continuously distilling collected liquid includes:

continuously supplying the collected liquid to a middle-stage section of the first distillation column.

9. The method according to claim 7, wherein said step of continuously distilling collected liquid includes:

leaving the distillate of the first distillation column to stand so that the distillate separates into an oleaginous layer and an aqueous layer.

10. The method according to claim 9, wherein said step of continuously distilling collected liquid further includes:

refluxing a part of the oleaginous layer to a column top of the first distillation column.

11. The method according to claim 7, wherein the bottom product of the first distillation column contains water, said method further comprising:

continuously distilling the bottom product of the first distillation column together with an azeotrope former which forms an azeotrope with water, by using a second distillation column, so that a distillate containing the azeotrope is obtained while the glycol ether is obtained as a bottom product.

12. The method according to claim 11, wherein said step of continuously distilling the bottom product includes:

continuously supplying the bottom product of the first distillation column to a middle-stage section of the second distillation column.

13. The method according to claim 11, wherein the azeotrope former has a boiling point lower than that of the glycol ether.

14. The method according to claim 11, wherein the azeotrope former is an organic compound which separates from water when an azeotrope of the organic compound and water is left to stand.

15. The method according to claim 11, wherein said step of continuously distilling the bottom product further includes:

leaving the distillate of the second distillation column to stand so that the distillate separates into an azeotrope former layer and an aqueous layer.

16. The method according to claim 15, wherein said step of continuously distilling the bottom product further includes:

refluxing a part of the azeotrope former layer to a column top of the second distillation column.

17. The method according to claim 1, wherein the glycol ether is a compound selected from the group consisting of 2-methoxyethanol, 2-ethoxyethanol, 2-n-propoxyethanol, 2-isopropoxyethanol, 2-n-butoxyethanol, 2-isobutoxyethanol, and 2-t-butoxyethanol.

18. The method according to claim 1, wherein the alkyl vinyl ether is a compound selected from the group consisting of methyl vinyl ether, ethyl vinyl ether, n-propyl vinyl ether, isopropyl vinyl ether, n-butyl vinyl ether, isobutyl vinyl ether, and t-butyl vinyl ether.

19. The method according to claim 11, wherein:

the glycol ether is 2-ethoxyethanol; and the azeotrope former is n-butanol.

* * * * *